United States Patent
Yamazaki et al.

(10) Patent No.: US 9,808,210 B2
(45) Date of Patent: Nov. 7, 2017

(54) PHOTON COUNTING TYPE X-RAY COMPUTED TOMOGRAPHY APPARATUS AND DATA TRANSFER METHOD FOR THE SAME

(71) Applicant: TOSHIBA MEDICAL SYSTEMS CORPORATION, Otawara-Shi (JP)

(72) Inventors: Takayuki Yamazaki, Nasushiobara (JP); Tomonori Ozaki, Otawara (JP); Jun Moteki, Otawara (JP); Makoto Ishizaki, Nasushiobara (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 595 days.

(21) Appl. No.: 14/243,393

(22) Filed: Apr. 2, 2014

(65) Prior Publication Data

US 2014/0211909 A1 Jul. 31, 2014

Related U.S. Application Data

(63) Continuation of application No. PCT/JP2013/077767, filed on Oct. 11, 2013.

(30) Foreign Application Priority Data

Oct. 17, 2012 (JP) ................. 2012-230088

(51) Int. Cl.
*A61B 6/03* (2006.01)
*A61B 6/00* (2006.01)
*G01N 23/04* (2006.01)

(52) U.S. Cl.
CPC ........... *A61B 6/032* (2013.01); *A61B 6/4241* (2013.01); *A61B 6/5205* (2013.01); *G01N 23/046* (2013.01); *A61B 6/482* (2013.01)

(58) Field of Classification Search
CPC ....... A61B 6/032; A61B 6/4241; A61B 6/482; A61B 6/5205; G01N 23/046
See application file for complete search history.

(56) References Cited

U.S. PATENT DOCUMENTS 4,751,587 A * 6/1988 Asahina ............... H04N 5/9262
348/415.1
2007/0205367 A1 9/2007 Deman et al.
(Continued)

FOREIGN PATENT DOCUMENTS

JP   2009-136437 A   6/2009
JP   2009-153829 A   7/2009
(Continued)

OTHER PUBLICATIONS

Leng et al., "Noise reduction in spectral CT: Reducing dose and breaking the trade-off between image noise and energy bin selection", Published Aug. 9, 2011, Medical Physics, vol. 38, No. 9, pp. 4946-4957.*

(Continued)

*Primary Examiner* — Glen Kao
(74) *Attorney, Agent, or Firm* — Oblon, McClelland, Maier & Neustadt, L.L.P.

(57) ABSTRACT

A photon counting type X-ray computed tomography apparatus includes an X-ray tube, a detector, a raw data generating section, an information compression section, and a data transmission section. The X-ray tube is configured to irradiate an X-ray. The detector is configured to count photons derived from the irradiated X-ray. The raw data generating section is configured to collect results of counting performed by the detector and to generate, from the results of counting, raw data for each of a plurality of energy bands. The information compression section is configured to compare values of the raw data between the raw data generated respectively for the energy bands, and to perform informa- (Continued)

tion compression of each of the raw data. The data transmission section is configured to transmit the raw data compressed by the information compression.

8 Claims, 7 Drawing Sheets

(56) References Cited

U.S. PATENT DOCUMENTS

| | | | | |
|---|---|---|---|---|
| 2009/0046913 A1* | 2/2009 | Chandra | ................ | A61B 6/035 382/131 |
| 2009/0140159 A1* | 6/2009 | Tomita | .................... | G01T 1/247 250/394 |
| 2010/0128949 A1* | 5/2010 | Wegener | ................... | G06T 9/00 382/131 |
| 2011/0096892 A1* | 4/2011 | Forthmann | ............ | A61B 6/032 378/5 |
| 2013/0251220 A1* | 9/2013 | Kraft | ..................... | G06T 11/003 382/128 |
| 2014/0192879 A1* | 7/2014 | Nakamura | ....... | H04N 19/00575 375/240.15 |

FOREIGN PATENT DOCUMENTS

| | | | |
|---|---|---|---|
| JP | 2009-207701 A | 9/2009 | |
| JP | 2010-201157 A | 9/2010 | |
| JP | 2012-034901 A | 2/2012 | |
| WO | WO 2012009725 A1 * | 1/2012 | ............. A61B 6/032 |

OTHER PUBLICATIONS

Chernoglazov, "Improving Visualization of Large Multi-Variate Datasets: New Hardware-Based Compression Algorithms and Rendering Techniques", Sep. 12, 2012, Master's Thesis, University of Canterbury, 119 pages.*
International Search Report dated Jan. 14, 2014 in PCT/JP2013/077767 filed Oct. 11, 2013 with English translation of categories.
International Preliminary Report on Patentability and Written Opinion dated Apr. 21, 2015 in PCT/JP2013/077767 (submitting English language translation only), Only y citation in English.
Combined Chinese Office Action and Search Report dated Oct. 26, 2015 in Patent Application No. 201380003672.1 (with English translation of categories of cited documents) Only search report indicating A references was in English.

* cited by examiner

PHOTON COUNTING TYPE X-RAY COMPUTED TOMOGRAPHY APPARATUS AND DATA TRANSFER METHOD FOR THE SAME

CROSS-REFERENCE TO RELATED APPLICATION

This application is a Continuation Application of No. PCT/JP2013/77767, filed on Oct. 11, 2013, and the PCT application is based upon and claims the benefit of priority from Japanese Patent Application No. 2012-230088, filed on Oct. 17, 2012, the entire contents of which are incorporated herein by reference.

FIELD

An embodiment of the present invention relates to a photon counting type X-ray computed tomography apparatus and a data transfer method for the same.

BACKGROUND

A conventional X-ray CT apparatus is configured to have an X-ray tube and an X-ray detector which are arranged opposite to each other on both sides of a subject P. Further, the X-ray detector is configured to have a plurality of channels of detecting elements arranged along a direction (channel direction) perpendicular to the longer side direction of a top plate, the longer side direction being the direction of the body axis of the subject.

Various types of X-ray detectors can be used for the X-ray CT apparatus. One of detectors being used for the X-ray CT apparatus in general is, for example, a scintillation detector. The scintillation detector includes a scintillator being a detecting element, and a photodiode being an optical sensor.

Further, an X-ray computed tomography apparatus (X-ray CT apparatus) using a photon counting type detector has been developed in recent years. The photon counting type detector is configured to individually count photons derived from X-rays transmitted through the subject. As for the photon counting type detector, there have been disclosed a technique counting photons derived from X-rays, for example, a semiconductor detector configured, by using a detecting element, to perform direct conversion of photons derived from X-rays incident on the detector, and a detector configured, by using a scintillator, a light guide, or a photomultiplier tube, to perform indirect conversion of the photons.

In the conventional techniques, a data collection apparatus using the photon counting type detector is configured such that a count value corresponding to the energy of an X-ray transmitted through the subject is acquired by individually counting photons derived from the X-rays transmitted through the subject. Further, the data collection apparatus is configured such that the energy region is divided into a plurality of regions, and such that the data based on the count values are collected for the respective divided energy regions.

However, in the case where the data collected by the data collection apparatus are transmitted and stored, and where the number of the divided energy regions is large, the amount of data is increased in proportion to the number of the divided energy regions.

For this reason, there is a problem that, in order to transfer (transmit) the collected data, it is necessary to secure a band for transferring the data and to increase the storage capacity of a storage apparatus.

DETAILED DESCRIPTION

A present embodiments provide a photon counting type X-ray computed tomography apparatus including: an X-ray tube configured to irradiate an X-ray; a detector configured to count photons derived from the irradiated X-ray; a raw data generating section configured to collect results of counting performed by the detector and to generate, from the results of counting, raw data for each of a plurality of energy bands; an information compression section configured to compare values of the raw data between the raw data generated respectively for the energy bands, and to perform information compression of each of the raw data; and a data transmission section configured to transmit the raw data compressed by the information compression.

Thereby, the photon counting type X-ray CT apparatus according to the present embodiment can transfer (transmit) collected data without securing the band for transmitting the data and increasing the storage capacity of the storage apparatus.

The photon counting type X-ray CT apparatus according to the present embodiment will be described with reference to the accompanying drawings.

The X-ray CT apparatus according to the present embodiment includes various types, such as a ROTATE/ROTATE type in which an X-ray tube and an X-ray detector are rotated as one body around a subject, and a STATIONARY/ROTATE type in which a large number of detection elements are arrayed in a ring-shape, and in which only the X-ray tube is rotated around the subject. The present invention can be applied to any one of these types. Here, the following description will be made on the assumption that the photon counting type X-ray CT apparatus is the ROTATE/ROTATE type which is a current mainstream.

Further, the mechanism for converting incident X-rays into electric charges includes an indirect conversion type in which X-rays are converted into photons by a fluorescent body such as a scintillator, and in which the photons are converted into electric charges by a photoelectric conversion element such as a photodiode, and a direct conversion type utilizing a photoconductive phenomenon in which electron-hole pairs are generated in a semiconductor by X-rays and moved to an electrode.

In addition, in recent years, a commercial product of a so-called multi-tube type X-ray CT apparatus, in which a plurality of pairs of the X-ray tube and the X-ray detector are mounted on a rotary ring, has been developed, and also the related technologies of the multi-tube type X-ray CT apparatus have been developed. The X-ray CT apparatus of the present embodiment can be applied to either of the conventional single-tube type X-ray CT apparatus, or the multi-tube type X-ray CT apparatus. Here, the following description will be made on the assumption that the X-ray CT apparatus of the present embodiment is the single-tube type X-ray CT apparatus.

Figure 1:
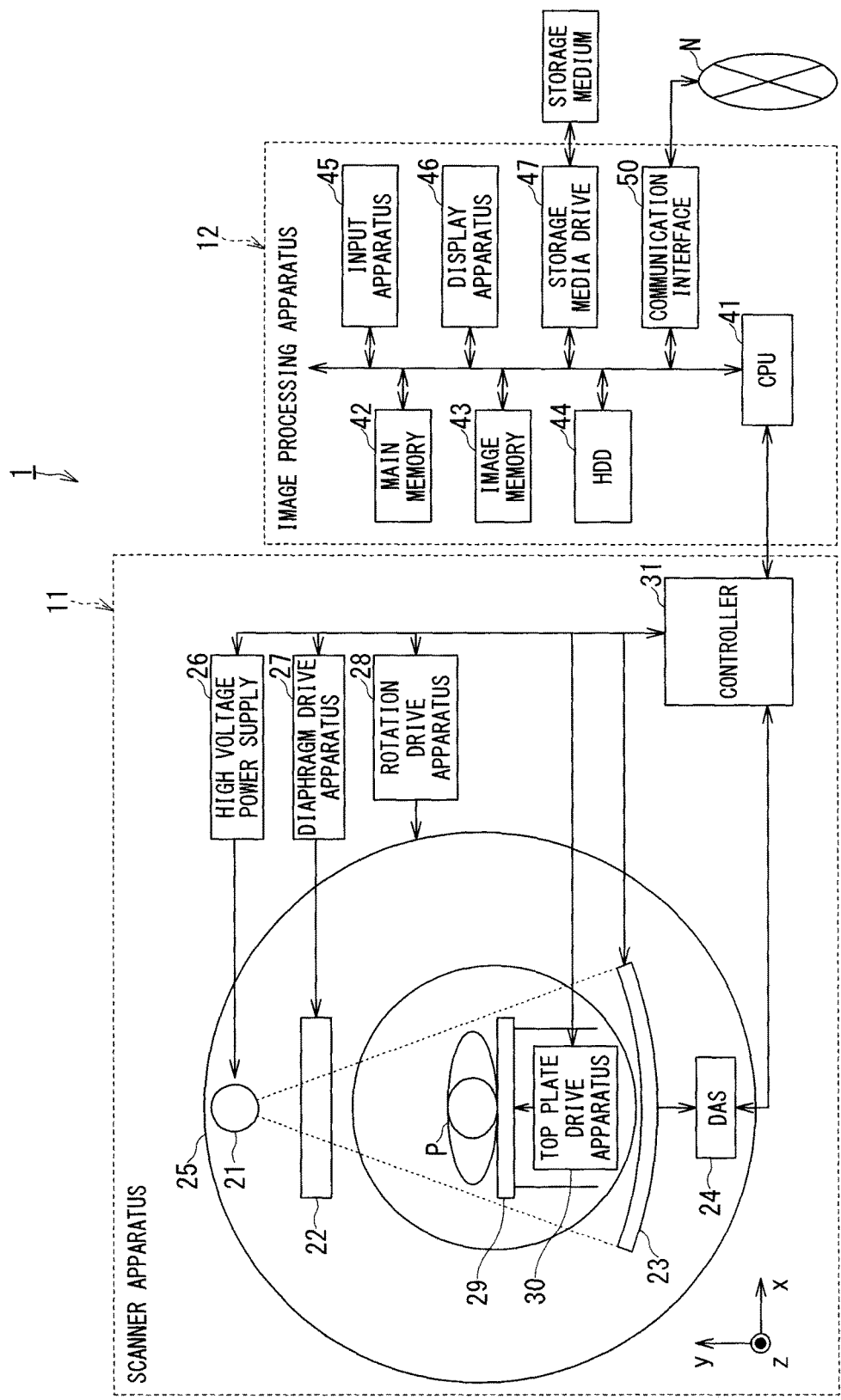
FIG. 1 is a view showing a hardware configuration of a photon counting type X-ray CT apparatus according to a present embodiment.

FIG. 1 is a view showing a hardware configuration of a photon counting type X-ray CT apparatus according to the embodiment.

As shown in FIG. 1, The X-ray CT apparatus 1 is mainly configured by a scanner apparatus 11 and an image processing apparatus 12.

The scanner apparatus 11 of the X-ray CT apparatus 1 is ordinarily installed in an examination room, and is configured to generate data of X-rays transmitted through a region of a patient (subject) P. On the other hand, the image processing apparatus 12 is ordinarily installed in a control room adjacent to the examination room, and is configured to generate projection data on the basis of the data of the transmitted X-rays and to perform generation and display of reconstructed images.

The scanner apparatus 11 of the X-ray CT apparatus 1 includes an X-ray tube 21, a diaphragm 22, a photon counting type detector (hereinafter simply referred to as "detector") 23, a DAS (Data Acquisition System) 24, a rotating section 25, a high voltage power supply 26, a diaphragm drive apparatus 27, a rotation drive apparatus 28, a top plate 29, a top plate drive apparatus 30 and a controller 31.

The X-ray tube 21 is configured to generate X-rays by colliding an electron beam with a metal target made of tungsten (W), and the like, according to a tube voltage supplied from the high voltage power supply 26, and to irradiate the generated X-rays to the detector 23. Fan beam X-rays or cone beam X-rays are formed by the X-rays irradiated from the X-ray tube 21. It should be noted that the electric power necessary for the irradiation of X-rays is supplied to the X-ray tube 21 from the high voltage power supply 26 under the control of the controller 31.

The diaphragm 22 is driven by the diaphragm drive apparatus 27 so as to adjust the slice-direction irradiation range of the X-rays irradiated from the X-ray tube 21. That is, the aperture of the diaphragm 22 is adjusted, by the diaphragm drive apparatus 27 so as to change the slice-direction irradiation range of the X-rays.

The detector 23 has a plurality of photon counting type detecting elements each configured to count photons derived from the X-rays transmitted through the subject P. The detector 23 is provided with a detecting element formed of, for example, cadmium telluride (CdTe). The detector 23 is configured as a direct conversion type semiconductor detector which counts photons derived from X-rays incident on the detector by a detecting element performing direct conversion of the photons derived from the X-rays.

It should be noted that the present embodiment is not limited to the semiconductor detector, and any detector capable of performing photon counting can be applied to the present embodiment. The detailed configuration of the detector 23 will be described below.

The detection signal detected by the detector 23 is transmitted to the DAS (Data Collection Apparatus) 24.

The DAS 24 is configured to measure the number of photons of the X-rays incident on the detector 23 for each of the energy regions of the X-rays by collecting the counting results of the detectors 23, and is also configured to generate raw data for each of the energy regions on the basis of the counting results and to apply information compression to the raw data. It should be noted that the detailed processing of the DAS 24 will be described below.

The rotating section 25 is configured to integrally hold the X-ray tube 21, the diaphragm 22, the detector 23, and the DAS 24. The rotating section 25 is configured to be able to rotate the X-ray tube 21, the diaphragm 22, the detector 23, and the DAS 24 integrally around the subject P in a state where the X-ray tube 21 and the detector 23 are arranged to face each other. It should be noted that the direction in parallel with the central rotation axis of the rotating section 25 is defined as the z-axis direction, and the two directions of the plane perpendicular to the z-axis direction are defined as the x-axis direction and the y-axis direction, respectively.

The high voltage power supply 26 is configured to supply the X-ray tube 21 with electric power necessary for the irradiation of X-rays under the control of the controller 31.

The diaphragm drive apparatus 27 has a mechanism which adjusts the X-ray irradiation range of the diaphragm 22 in the slice-direction under the control of the controller 31.

The rotation drive apparatus 28 has a mechanism which rotates the rotating section 25 under the control of the controller 31 so that the rotating section 25 rotates around a cavity section (opening section) thereof in a state where the positional relationship in the rotating section 25 is maintained.

The top plate 29 is configured to mount the subject P thereon.

The top plate drive apparatus 30 has a mechanism which, under the control of the controller 31, moves the top plate 29 vertically along the y-axis direction, and moves the top plate 29 into and out of the opening section along the z-axis direction, and has a mechanism which shifts the top plate 29 in the x-axis direction. The rotating section 25 has the opening section in the center portion thereof, and is configured such that the subject P mounted on the top plate 29 is inserted into the opening section.

The controller 31 is configured by a CPU (Central Processing Unit) and a memory. The controller 31 performs control of the detector 23, the DAS 24, the high voltage power supply 26, the diaphragm drive apparatus 27, the rotation drive apparatus 28, the top plate drive apparatus 30, and the like, so that the scanning operation is performed. Further, the controller 31 is configured to transmit, to the image processing apparatus 12, raw data compressed by information compression in the DAS 24.

The image processing apparatus 12 of the photon counting type X-ray CT apparatus 1 has a computer-based configuration and can perform interactive communication via a trunk network N, such as a LAN (Local Area Network), in a hospital. The image processing apparatus 12 is mainly configured by basic hardware components, such as a CPU 41, a main memory 42, an image memory 43, an HDD (Hard Disc Drive) 44, an input apparatus 45, a display apparatus 46, a communication interface 50, and the like.

The CPU 41 is mutually connected with the respective hardware components configuring the image processing apparatus 12 via a bus being a common signal transmission path. It should be noted that, in some cases, the image processing apparatus 12 includes a storage media drive 47.

The CPU 41 is a control device configured as an integrated circuit (LSI) in which electronic circuits composed of semiconductor devices are housed in a package having a plurality of terminals. When an instruction is inputted, for example, by an operation of the input apparatus 45 performed by an operator, such as a doctor or a medical technician, the CPU 41 starts to execute a program stored in the main memory 42. Alternatively, the CPU 41 loads the main memory 42 with a program stored in the HDD 44, a program transferred from the network N and installed in the HDD 44, or a program installed in the HDD 44 after being read from a storage medium mounted to the storage media drive 47, and then executes the loaded program.

The main memory 42 is a storage device including a ROM (Read Only Memory), a RAM (Random Access Memory), and the like. The main memory 42 stores an IPL (Initial Program Loading), a BIOS (Basic Input/Output System) and data, and is used as a work memory of the CPU 41 and a memory for temporary data storage.

The image memory 43 is a storage device which stores generated raw data and reconstructed image data.

The HDD 44 is a storage device having a configuration in which a metal disk with a magnetic body coated or deposited thereon is undetachably provided. The HDD 44 is a storage device which stores therein data and programs (including an OS (Operating System), and the like, in addition to an application program) installed in the image processing apparatus 12. Further, the HDD 44 needs only to be a storage device and may have a form using an SSD (Solid State Drive) configured by a semiconductor memory.

The input apparatus 45 is a pointing device or a keyboard which can be operated by the operator. The input signal according to the operation of the operator is sent to the CPU 41.

The display apparatus 46 includes an image synthesizing circuit, a VRAM (Video Random Access Memory), a display, and the like, which are not shown. The image synthesizing circuit generates synthesized data by synthesizing image data with text data of various parameters, and the like. The VRAM expands the synthesized data to display image data to be displayed on the display. The display is configured by a CRT (Cathode Ray Tube), a LCD (Liquid Crystal Display), or the like, and displays the display image data successively as display images.

The storage media drive 47 is configured to be detachably provided with a storage medium and is configured to read data (including a program) stored in the storage medium so as to output the read data onto the bus, and to write data supplied via the bus into the storage medium.

The communication interface 50 is an interface section configured to perform transmission and reception of image data and communication via the network N.

The image processing apparatus 12 applies correction processing (preprocessing), such as logarithmic conversion processing and sensitivity correction, to the raw data inputted from the DAS 24 of the scanner apparatus 11 via the controller 31, so as to generate projection data. Further, the image processing apparatus 12 applies scattered ray elimination processing to the preprocessed projection data. The image processing apparatus 12 generates a reconstructed image as data by reconstructing the projection data subjected to the scattered ray elimination processing, and stores the generated data in the image memory 43.

Figure 2:
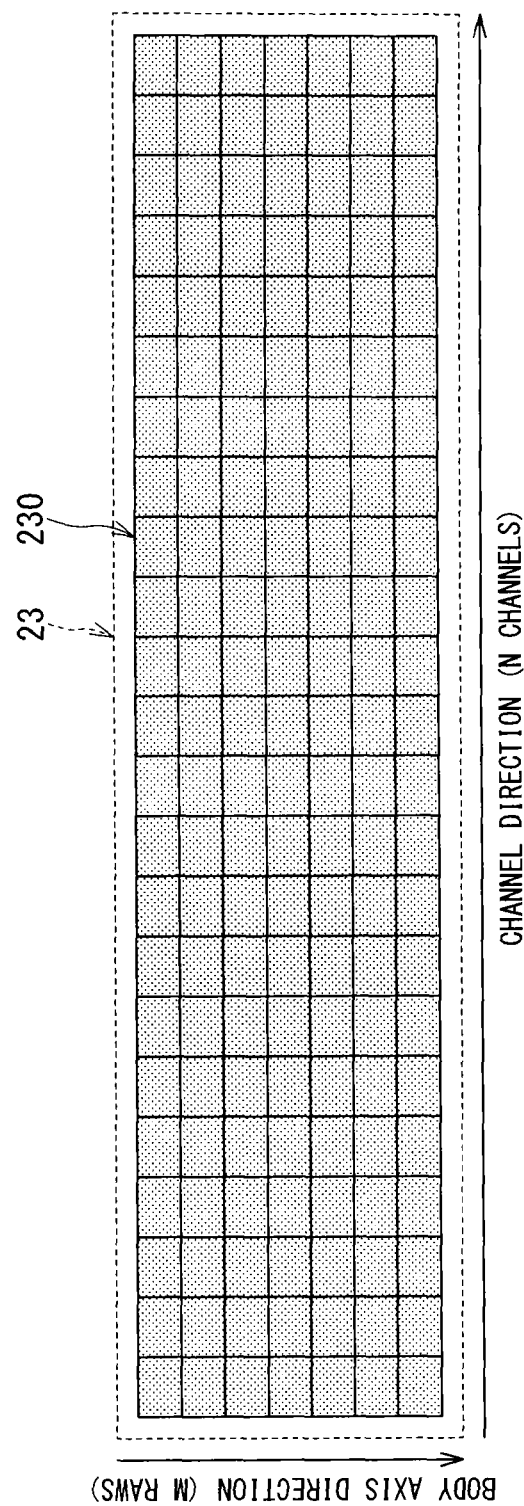
FIG. 2 is a view showing a configuration of a detector according to the present embodiment.

FIG. 2 is a view showing a configuration of the detector 23 according to the present embodiment.

As shown in FIG. 2, in the detector 23, detecting elements 230, each configured by a cadmium telluride semiconductor (CdTe, CdZnTe, and the like), are arranged in a plurality of channels (N channels) in the channel direction and in a plurality of rows (M rows) in the slice direction (body axis direction). The detector 23 is configured to count photons derived from incident X-rays by directly converting the X-rays into photons by the detecting elements 230. Further, the detector 23 is configured to discriminate the energy value of the transmitted X-ray. It should be noted that, even when the detector 23 is configured by a scintillator, a light guide, and a photomultiplier tube, the detector is applicable for counting photons.

Figure 3:
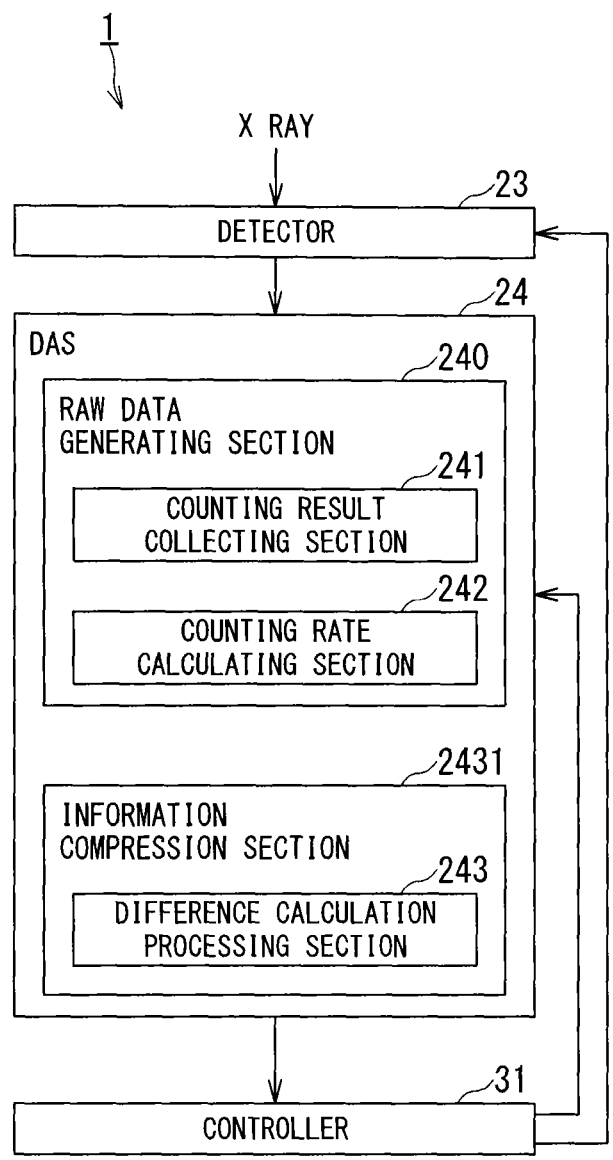
FIG. 3 is a functional block diagram for mainly explaining functions of a DAS of the present embodiment.

FIG. 3 is a functional block diagram for mainly explaining the functions of the DAS 24 of the present embodiment.

As shown in FIG. 3, the DAS 24 is provided with a raw data generating section 240 and an information compression section 2431.

The raw data generating section 240 is configured to collect the results of counting performed by the detector 23 and to generate raw data of a plurality of energy bands from the counting results. Specifically, the raw data generating section 240 includes a counting result collecting section 241 and a counting rate calculating section 242.

The counting result collecting section 241 collects the counting results of the detector 23, that is, an energy value for each detection time, at which each photon derived from an X-ray transmitted through the subject P is detected, for each detection position (position of the detecting element 230), and for each phase (tube phase) of the X-ray tube 21.

It should be noted that, since the detector 23 can discriminate the energy values, it is assumed that the counting result collecting section 241 handles, as the counting results, the detection time, the X-ray energy value, and the detection position.

The counting rate calculating section 242 is configured, for each X-ray energy value, to calculates (collects), as a value based on the counting results of the detector 23, a value (a counting rate or a count value) representing the number of counts of photons derived from X-rays, the photons being counted by each of the detecting elements 230 of the detector 23 per unit time.

Thereby, the counting result collecting section 241 and the counting rate calculating section 242 are configured to generate raw data of a plurality of energy bands on the basis of the collected results, that is, on the basis of the photon detection time, the detection position of the detecting element 230, the tube phase, the energy value, and the count value.

The information compression section 2431 is configured to apply information compression to the raw data generated by the raw data generating section 240. As the information compression method applied by the information compression section 2431, it is possible to apply any of the information compression methods such as, for example, DPCM (Differential Pulse Code Modulation), wavelet transformation, DCT (Discrete Cosine Transformation), and delta compression (differential encoding).

In the information compression method, the compression effect is generally high because, after transformation (compression) is performed by referring to similar data, the frequency of occurrence of specific data becomes high. For this reason, a high compression ratio can be obtained by referring to the counting rate or the count value between the raw data of a plurality of energy bands. Here, one of specific methods used for referring to the counting rate or the count value between the raw data of energy bands is, for example, a difference calculation processing method.

The information compression section 2431 is configured to include a difference calculation processing section 243 in order to realize the difference calculation processing method. It should be noted that the information compression section 2431 may be provided with a desired information compression processing section adopting any information source encoding system other than the difference calculation processing method.

The difference calculation processing section 243 is configured to select one energy band of the plurality of energy bands as a reference energy band to set the raw data of the selected reference energy band as reference data, and on the other hand, is configured, for the energy bands other than the reference energy band, to obtain difference data between the raw data of two energy bands adjacent to each other. Further, the difference calculation processing section 243 is configured to send out the obtained reference data and a plurality of the obtained difference data to the controller 31.

It should be noted that, in the present embodiment, not being limited to the number of energy bands, the difference calculation processing section 243 can calculate reference data of the reference energy band, and difference data between the raw data of two energy bands adjacent to each other, respectively. Therefore, in the present embodiment, the amount of data can be significantly reduced as compared with the case where all of the raw data are transmitted or where all of the raw data are stored.

For example, the difference data between raw data of two energy bands adjacent to each other can be continuously calculated in such a manner that a difference between the reference data and the raw data of the first energy band located adjacent to the reference energy band of the reference data is set as first difference data, and that a difference between the raw data of the first energy band having the first difference data, and the raw data of the second energy band located adjacent to the first energy band is set as second difference data. Further, in the present embodiment, the direction of calculation of the difference data of two energy bands adjacent to each other is not limited to one of the positive and negative directions originating from the reference energy band. The difference data of two energy bands adjacent to each other can be calculated in both the directions originating from the reference energy band.

The controller 31 (data transmission section) is provided with a function of transmitting the reference data and the plurality of difference data which are calculated in the difference calculation processing section 243. Further, the controller 31 is configured to control the dose of X-ray irradiation from the X-ray tube 21 on the basis of the results of calculation performed by the counting rate calculating section 242.

Figure 4:
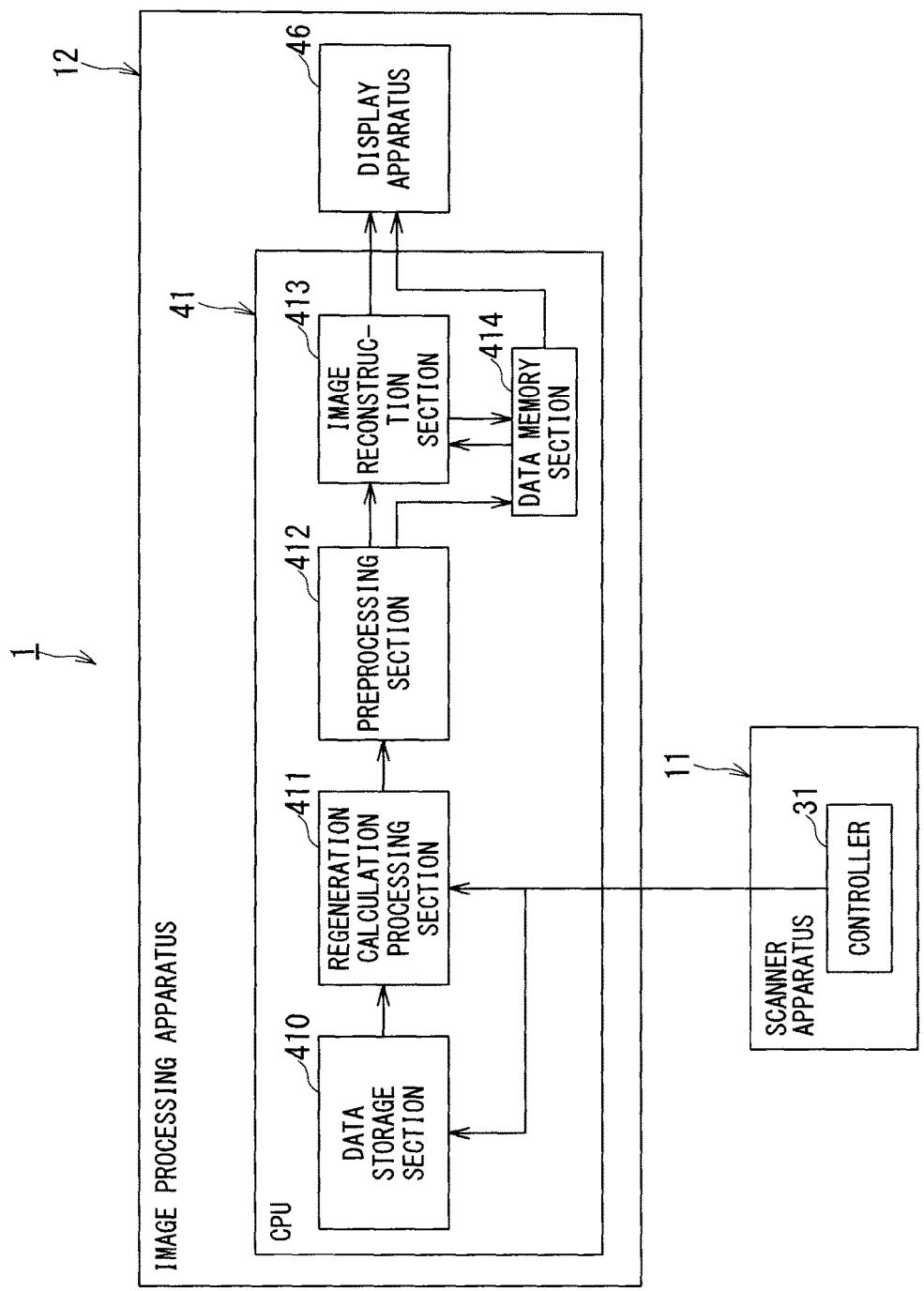
FIG. 4 is a functional block diagram showing functions of an image processing apparatus of the photon counting type X-ray CT apparatus according to the present embodiment.

FIG. 4 is a functional block diagram showing functions of the image processing apparatus 12 of the photon counting type X-ray CT apparatus 1 of the present embodiment.

The CPU 41 shown in FIG. 1 executes various programs stored in the main memory 42, and thereby the image processing apparatus 12 is made to function as a data storage section 410, a regeneration calculation processing section 411, a preprocessing section 412, an image reconstruction section 413, and a data memory section 414. It should be noted that each of the data storage section 410 and the data memory section 414 may have a form configured by the image memory 43 or the HDD 44.

The data storage section 410 is configured to store the reference data and the plurality of difference data transmitted from the controller 31 of the scanner apparatus 11. It should be noted that it is not necessary to provide the data storage section 410 in the case where the reference data and the plurality of difference data are not stored, and the raw data are regenerated by using, as they are, the received reference data and the plurality of received difference data.

The regeneration calculation processing section 411 is configured to regenerate the raw data of the plurality of energy bands on the basis of the received reference energy and the plurality of received difference data.

The preprocessing section 412 is configured to perform processing in which the raw data regenerated by the regeneration calculation processing section 411 are processed to be used for the reconstruction. Specifically, the preprocessing section 412 is configured to generate projection data by applying, to the raw data, correction processing, such as logarithmic conversion processing, offset correction, sensitivity correction, and beam hardening correction according to the counting result transmitted from the counting result collecting section 241, and the settings set in the input apparatus 45 by the operator. The generated projection data is stored in the data memory section 414.

The image reconstruction section 413 reconstructs an X-ray CT image by applying back projection processing (for example, back projection processing based on the FBP (Filtered Back Projection) method) to the generated projection data. The image reconstruction section 413 stores the reconstructed X-ray CT image in the data memory section 414. It should be noted that the projection data to be subjected to the reconstruction processing may be directly acquired from the preprocessing section 412, and when the projection data is stored in the data memory section 414, the stored projection data may be used.

The data memory section 414 is configured to store the reconstructed X-ray CT image. Further, the data to be stored in the data memory section 414 is not limited to the X-ray CT image. For example, the projection data generated in the preprocessing section 412 may be stored in the data memory section 414, or the projection data for generating a scanogram may also be stored in the data memory section 414.

The display apparatus 46 is configured to display the X-ray CT image and the scanogram which are stored in the data memory section 414, on the basis of an instruction inputted from the input apparatus 45 by the operator, such as a doctor or a medical technician.

As described above, the photon counting type X-ray CT apparatus 1 according to the present embodiment is configured such that the DAS 24 generates raw data of a plurality of energy bands. The difference calculation processing section 243 of the DAS 24 is configured to select one energy band of the plurality of energy bands as a reference energy band to set the raw data of the selected reference energy band as reference data, and on the other hand, is configured, for the energy bands other than the reference energy band, to obtain difference data between the raw data of two energy bands adjacent to each other. Further, the difference calculation processing section 243 is configured to send out the obtained reference data and a plurality of the obtained difference data to the controller 31.

In this way, in the case where, in the photon counting type X-ray CT apparatus 1 according to the present embodiment, the raw data are transmitted from the scanner apparatus 11 to the image processing apparatus 12, only the obtained reference data and the plurality of obtained difference data are transmitted, so that the image processing apparatus 12 can regenerate the raw data on the basis of the reference data and the plurality of difference data.

Thereby, in the photon counting type X-ray CT apparatus 1 according to the present embodiment, when data collected by the DAS 24 are transmitted (transferred) and stored, the obtained reference data and a plurality of the obtained difference data are transmitted, and hence the amount of raw data to be transmitted can be made smaller (reduced) as compared with the amount of conventional raw data. As a result, it is possible to avoid the necessity of securing the band for transmitting (transferring) the data, and the necessity of increasing the storage capacity of the storage apparatus.

It should be noted that the difference data is data representing the difference between raw data of energy bands adjacent to each other, and hence, per unit energy band, the amount of the difference data is smaller than the amount of the raw data.

Therefore, the photon counting type X-ray CT apparatus 1 according to the present embodiment is configured to transmit the reference data and a plurality of the difference data and thereby can significantly reduce the amount of data to be transmitted, as compared with the apparatus which transmits the raw data for each energy band.

Thereby, in the photon counting type X-ray CT apparatus 1 according to the present embodiment, even when the number of energy bands is increased, it is not necessary to secure the band for transmitting the data and to increase the storage capacity of the storage apparatus for storing the raw data, and hence space saving can be achieved.

(Data Transmission Processing)

Next, there will be described data transmission processing in which the scanner apparatus 11 of the photon counting type X-ray CT apparatus 1 according to the present embodiment transmits reference data and a plurality of difference data.

Figure 5:
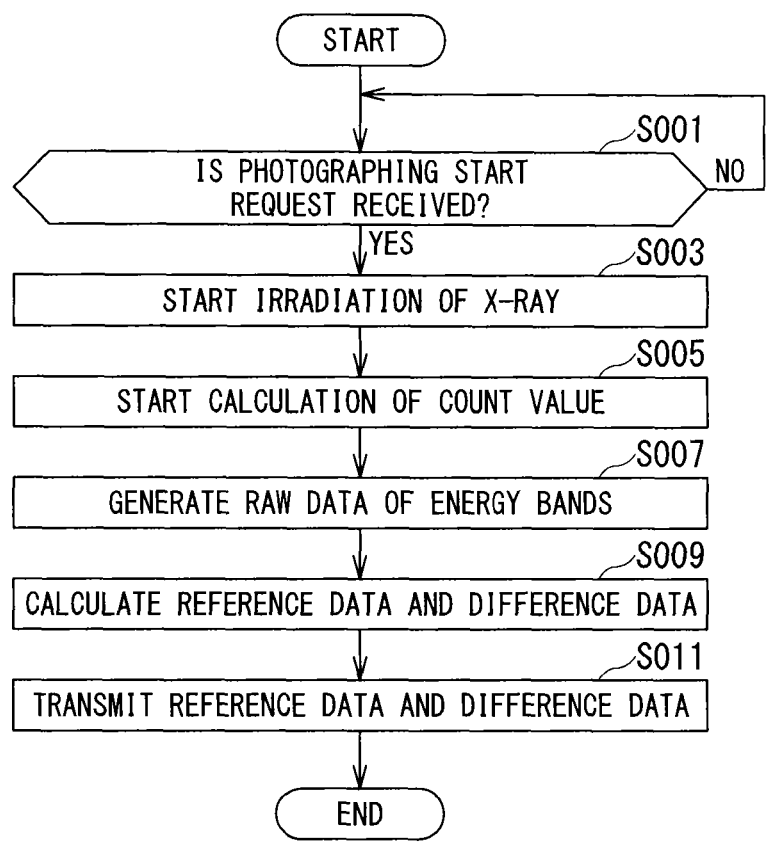
FIG. 5 is a flow chart showing a data transmission processing procedure by which a scanner apparatus of the photon counting type X-ray CT apparatus according to the present embodiment transmits reference data and a plurality of difference data.

FIG. 5 is a flow chart showing a data transmission processing procedure by which the scanner apparatus 11 of the photon counting type X-ray CT apparatus 1 according to the present embodiment transmits reference data and a plurality of difference data.

As shown in FIG. 5, the photon counting type X-ray CT apparatus 1 according to the present embodiment determines whether or not an operator's request for starting the photographing of an X-ray CT image is received via the input apparatus 45 (step S001). Here, when the photographing start request is not received (step S001: No), the photon counting type X-ray CT apparatus 1 waits until it receives the photographing start request (step S001).

On the other hand, when the photographing start request is received (step S001: Yes), the X-ray tube 21 is made to start irradiation of X-rays to the detector 23 by the control of the controller 31 via the high voltage power supply 26 (step S003).

Next, the counting rate calculating section 242 of the DAS 24 starts calculation of a value (for example, a count value) representing the number of counts of photons derived from X-rays which are detected by each of the detecting elements 230 of the detector 23 per unit time (Step S005).

The counting result collecting section 241 collects, for each tube phase of the X-ray tube 21, the detection time and position at which a photon derived from each of X-rays transmitted through the subject P is detected. It should be noted that the detector 23 can perform discrimination based on energy values and hence collects, as the counting results, the detection time, the X-ray energy values, and the detection positions. Then, the raw data generating section 240 generates raw data of a plurality of energy bands from the collected counting results (step S007).

Here, the raw data generating section 240 may be configured to generate raw data of a plurality of energy bands according to threshold values of energy. Specifically, on the basis of differences between characteristics of X-rays transmitted through the subject P, a threshold value may be set for each energy band of the X-rays so as to enable the energy discrimination to be performed on the basis of the threshold values.

Specifically, when the energy values of X-rays are measured, an element can be specified from the characteristics of the measured energy values. For example, when the threshold values corresponding to the characteristics of the element are set for energy values, raw data based on the count values can be generated in the energy bands in which the threshold values are set. In this case, in order to distinguish calcium, uric acid, and a cancer cell, raw data can be generated by dividing the energy band on the basis of the threshold values corresponding to these elements.

On the basis of the raw data generated by the raw data generating section 240, the difference calculation processing section 243 selects one of the plurality of energy bands as a reference energy band and sets the raw data of the selected reference energy band as reference data. For the energy bands other than the reference energy band, the difference calculation processing section 243 calculates and obtains difference data between the raw data of two energy bands adjacent to each other (step S009). The calculation method of the difference data will be described with reference to a drawing.

Figure 6:
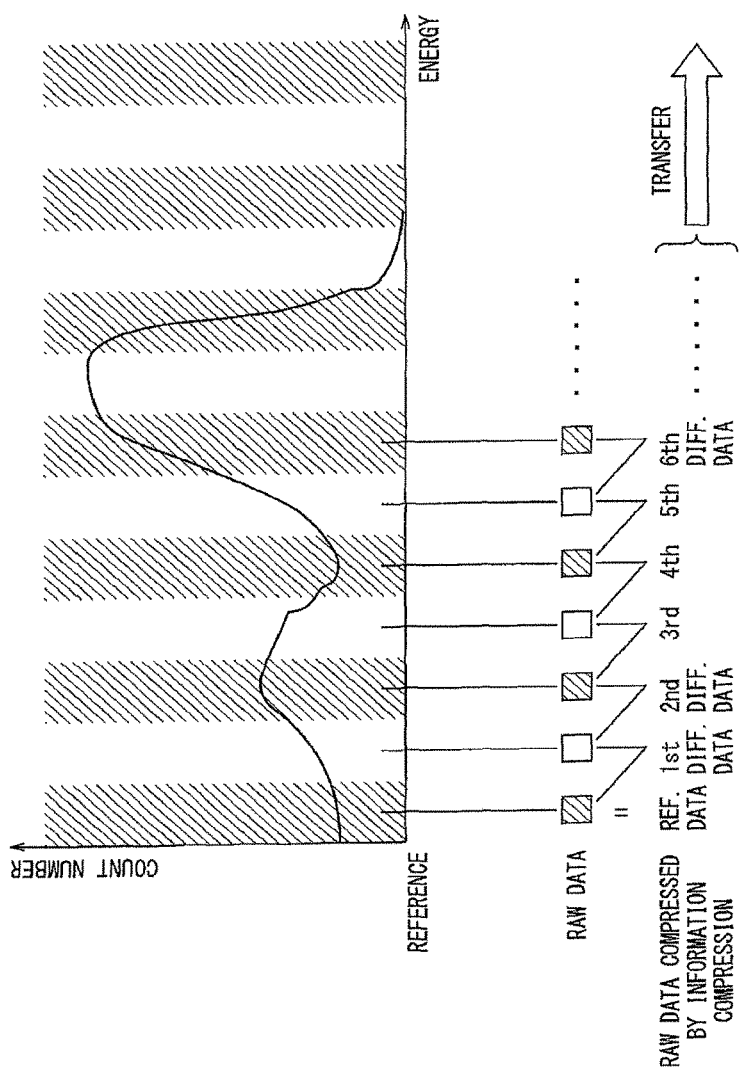
FIG. 6 is an illustration for explaining a case where a difference calculation processing section according to the present embodiment calculates reference data and a plurality of difference data from raw data.

FIG. 6 is an illustration for explaining a case where the difference calculation processing section 243 according to the present embodiment calculates reference data and a plurality of difference data from raw data.

From the raw data generated by the raw data generating section 240, the difference calculation processing section 243 calculates reference data and a plurality of difference data on the basis of the count value of each of the energy bands. For example, in FIG. 6, the difference calculation processing section 243 divides the energy region into a plurality of energy bands, and calculates a count value of each of the predetermined detecting elements 230 at a predetermined time point. Then, when setting the energy band with a minimum energy value as a reference energy band, the difference calculation processing section 243 calculates, as first difference data, the difference between the count value of the reference energy band and the count value of the energy band adjacent to the reference energy band.

Subsequently, the difference calculation processing section 243 calculates second difference data representing the difference between the count value used to calculate the first difference data and the count value of the energy band adjacent to the energy band whose count value is used to calculate the first difference data. In this way, the difference calculation processing section 243 calculates difference data between the count values for each of the continuously formed energy bands (that is, calculates difference data between the count values of two energy bands adjacent to each other).

Figure 7:
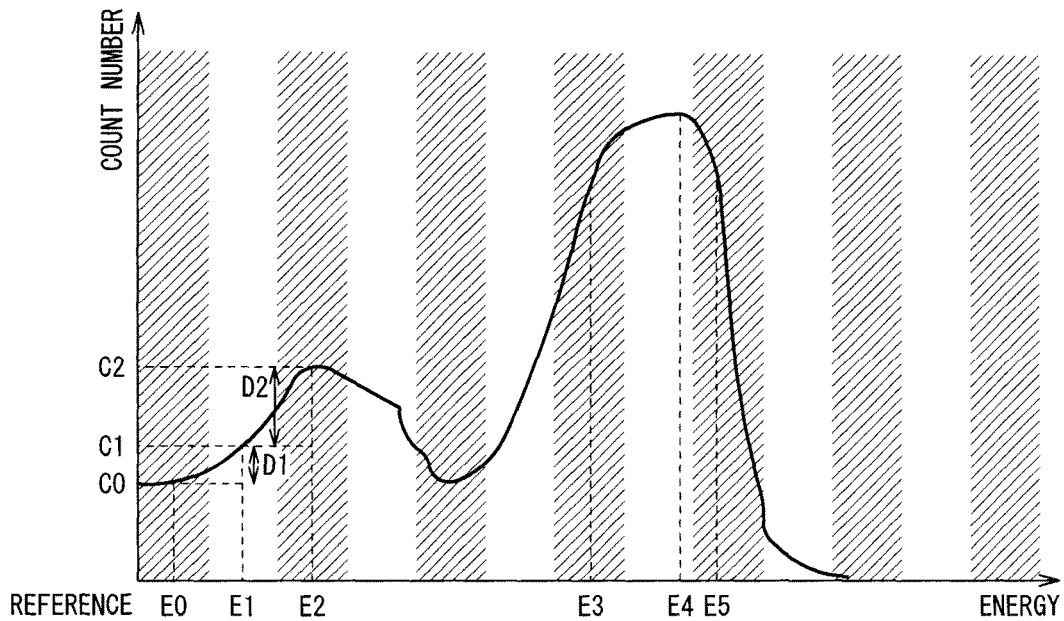
FIG. 7 is an illustration for explaining difference data calculated by the difference calculation processing section according to the present embodiment.

FIG. 7 is an illustration for explaining difference data calculated by the difference calculation processing section 243 according to the present embodiment.

As shown in FIG. 7, for example, when an energy band E0 is set as a reference energy band, a count value C0 is set as reference data. Further, difference data D1 (first difference data) of an energy band E1 corresponds to the difference obtained by subtracting the count value C0 of the reference energy band E0 from the count value C1 of the energy band E1. Similarly, difference data D2 (second difference data) of an energy band E2 corresponds to the difference obtained by subtracting the count value C1 of the energy band E1 from the count value C2 of the energy band E2.

When the difference calculation processing section 243 completes the calculation of difference data of two energy bands adjacent to each other for each of the energy bands, the controller 31 transmits, to the image processing apparatus 12, the reference data and the plurality of difference data calculated for each of the energy bands (step S011).

As described above, in the photon counting type X-ray CT apparatus 1 according to the present embodiment, the raw data generating section 240 generates raw data in a plurality of energy bands. Further, the difference calculation processing section 243 calculates reference data of a reference energy band set as a reference, and calculates difference data of two mutually adjacent energy bands for each of the energy bands. Then, the difference calculation processing section 243 transmits the reference data and the plurality of difference data via the controller 31.

Thereby, in the photon counting type X-ray CT apparatus 1 according to the present embodiment, the raw data can be reconstructed by the image reconstruction section 413 of the image processing apparatus 12 only by transmitting the reference data and the plurality of difference data from the scanner apparatus 11.

It should be noted that, in the data transmission processing procedure described above, the difference calculation processing section 243 calculates difference data between mutually adjacent energy bands for each of the energy bands, but the method for determining the energy band width at the time of calculating the difference data is not limited to this. Specifically, the reference energy band may be changed on the basis of an absorption rate or scattering rate of X-rays, the rates being represented by counting results. That is, the energy band may be changed on the basis of the characteristics represented by the count values.

Generally, it is known that when X-rays are irradiated to a substance, a part of the X-rays are transmitted, and a part of the X-rays are absorbed, and that a part of the X-rays are reflected and scattered. In a classical atomic model, when X-rays are irradiated to an atom, excess energy is emitted as X-rays, or photons are transmitted through or absorbed in the atom depending on energy levels specific to the electrons of the atom. Further, in the relationship between the photon energy and the electron binding energy, when the photon energy is slightly higher than the electron binding energy, the photon is absorbed, and when the photon energy is lower than electron binding energy, a K-edge, a jump, or the like, can occur. For this reason, the energy band may be changed on the basis of a change in the count value corresponding to the energy value (a change in the intensity of energy).

For example, in FIG. 7, the count value in the range of the energy value E3 to the energy value E4 changes substantially linearly. Similarly, the count value in the range of the energy value E4 to the energy value E5 changes substantially linearly. In this way, on the basis of the absorption rate or scattering rate of X-rays represented by the count values, the range from the energy value E3 to the energy value E4 may be set as an energy band, and the range from the energy value E4 to the energy value E5 may be set as an energy band.

Further, the difference calculation processing section 243 may be configured to change the energy band on the basis of characteristics specific to an element. In this case, on the basis of characteristics specific to an element, the difference calculation processing section 243 may divide the energy band into three bands of a band of 35 keV to 70 keV, a band of 70 keV to 140 keV, and a band of 140 keV or more, so as to perform the energy discrimination. It should be noted that, in this case, any one of the three energy bands may be set as the reference energy band.

Further, since the absorption rate or scattering rate of X-rays is changed by a contrast agent, the difference calculation processing section 243 may be configured to change the energy bands according to the contrast agent to be used or a combination of contrast agents.

Further, the difference calculation processing section 243 may be configured to set a plurality of reference energy bands on the basis of the raw data generated by the raw data generating section 240. In this case, for example, the difference calculation processing section 243 can select, as reference data, the count value of the raw data of any one of the plurality of set reference energy bands, and can calculate difference data between the mutually adjacent energy bands each formed continuously from the reference energy band of the selected reference data. In this case, when a plurality of reference energy bands are set, the value of the difference data calculated in each of the energy bands can be made small, so as to reduce the amount of data.

Further, the difference calculation processing section 243 may be configured to change and determine the energy band according to a change in the count value. For example, it is also possible that, in the energy region in which the change in the count value is small, the difference calculation processing section 243 increases the width of the energy band, and that, in the energy region in which the change in the count value is large, the difference calculation processing section 243 reduces the width of the energy band.

It should be noted that, when transmitting reference data and a plurality of difference data to the image processing apparatus 12 in step S011, the controller 31 may transmit the data after applying a general compression technique to the data to compress the data, or may calculate difference data between the detecting elements 230 and transmit the difference data between the detecting elements 230 adjacent to each other in the same energy band.

(Data Reception Reconstruction Processing)

Next, there will be described processing in which reference data and a plurality of difference data transmitted by the scanner apparatus 11 of the X-ray CT apparatus 1 are received, and in which raw data is regenerated from the reference data and the plurality of difference data, so as to reconstruct projection data.

Figure 8:
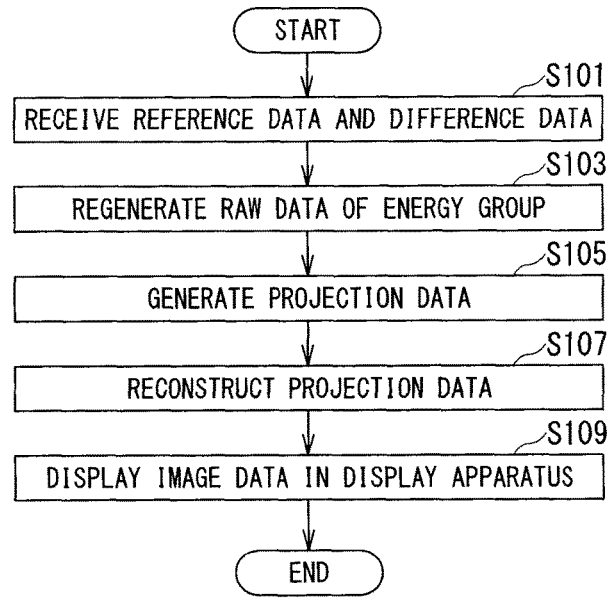
FIG. 8 is a flow chart showing data reception reconstruction processing procedure by which an image processing apparatus of the photon counting type X-ray CT apparatus according to the present embodiment performs reception of the reference data and the plurality of difference data, regeneration of raw data from the reference data and the plurality of difference data, and reconstruction of projection data.

FIG. 8 is a flow chart showing data reception reconstruction processing procedure by which the image processing apparatus 12 of the photon counting type X-ray CT apparatus 1 according to the present embodiment receives reference data and a plurality of difference data, and regenerates raw data from the reference data and the plurality of difference data, so as to reconstruct projection data.

As shown in FIG. 8, the image processing apparatus 12 according to the present embodiment receives, via the controller 31 of the scanner apparatus 11, reference data and a plurality of difference data which are calculated in the difference calculation processing section 243 (step S101). The CPU 41 of the image processing apparatus 12 stores, in the data storage section 410, the received reference data and the plurality of received difference data.

On the basis of the reference data and the plurality of difference data which are received from the scanner apparatus 11, the regeneration calculation processing section 411 regenerates the raw data generated by the raw data generating section 240 (step S103). The regeneration calculation processing section 411 transmits the regenerated raw data to the preprocessing section 412.

The preprocessing section 412 receives the raw data regenerated in the regeneration calculation processing section 411. The preprocessing section 412 applies, to the received raw data, correction processing, such as logarithmic conversion processing, offset correction, sensitivity correction, and beam hardening correction, according to the counting result transmitted from the counting result collecting section 241, and an operator's instruction from the input apparatus 45. The preprocessing section 412 generates projection data from the raw data by performing the correction processing (step S105). Here, the preprocessing section 412 may be configured to store the generated projection data in the data memory section 414.

The image reconstruction section 413 applies back projection processing to the projection data generated by the preprocessing section 412, or to the projection data stored in the data memory section 414, so as to reconstruct an X-ray CT image (step S107). The image reconstruction section 413 stores the reconstructed X-ray CT image in the data memory section 414.

It should be noted that the data stored in the data memory section 414 is not limited to the X-ray CT image subjected to the energy discrimination. The data memory section 414 may be configured to store, for example, the projection data generated in the preprocessing section 412 and the projection data for generating a scanogram.

On the basis of on an operator's instruction inputted from the input apparatus 45, the display apparatus 46 displays the X-ray CT image subjected to the energy discrimination and the scanogram which are stored in the data memory section 414 (step S109).

As described above, from reference data and a plurality of difference data which are transmitted from the scanner apparatus 11, the image processing apparatus 12 of the photon counting type X-ray CT apparatus 1 according to the present embodiment regenerates the raw data detected by the detector 23. That is, in the photon counting type X-ray CT apparatus 1 according to the present embodiment, the reference data and the plurality of difference data are transmitted to the image processing apparatus 12 from the scanner apparatus 11, so that the image processing apparatus 12 can regenerate the raw data.

Thereby, in the image processing apparatus 12 of the photon counting type X-ray CT apparatus 1 according to the present embodiment, the image reconstruction section 413 performs the reconstruction processing on the basis of the regenerated raw data, so that the display apparatus 46 can display the X-ray CT image (image data) subjected to the energy discrimination.

It should be noted that the image processing apparatus 12 according to the present embodiment is not limited to a configuration in which the image processing apparatus 12 is integrated with the photon counting type X-ray CT apparatus 1. For example, the image processing apparatus 12 may be installed at a distant place different from the installation place of the scanner apparatus 11, so as to function in a cloud computing environment.

Further, the display apparatus 46 may be configured such that, when displaying, in step S109, the X-ray CT image subjected to the energy discrimination, the display apparatus 46 displays, as a synthesized image, an image obtained by combining X-ray CT images subjected to desired energy discrimination.

Although a couple of embodiments of the invention are explained, these embodiments are exemplary only and it is not intended that the scope of the invention is limited by the embodiments. These embodiments can be put into practice in other various forms, and can be variously omitted, replaced or changed within the scope of the invention. The embodiments and their modifications are included in the scope and the coverage of the invention, and similarly in the equivalents to the claimed invention.

Also, in the embodiments of the present invention, the steps of flow charts show example processes that are performed in time-series in the order described, but they may also include processes that can be performed in parallel or independently rather than being performed in time-series.

What is claimed is:

1. A photon counting type X-ray computed tomography apparatus comprising:
    an X-ray tube configured to irradiate an X-ray;
    a detector configured to count photons derived from the irradiated X-ray;
    a raw data generating section configured to collect results of counting performed by the detector and to generate, from the results of counting, raw data for each of a plurality of energy bands;
    an information compression section including a difference calculation processing section that is configured to
        select, for each energy range of energy ranges, one of the plurality of energy bands belonging to the corresponding each energy range as a reference energy band, the energy ranges being divided into the each energy range at an energy where a change amount of count value exceeds a threshold,
        set raw data of the reference energy band for the each energy range as reference data for the each energy range, and
        perform, for the each energy range, information compression of multiple pieces of raw data for energy bands other than the reference energy band by obtaining corresponding multiple pieces of difference data, each piece of difference data being difference between raw data of respective two adjacent energy bands belonging to the corresponding each energy range; and
    a data transmission section configured to transmit the multiple pieces of difference data and the reference data as raw data compressed by the information compression.

2. The photon counting type X-ray computed tomography apparatus according to claim 1, wherein
    on the basis of the generated raw data, the difference calculation processing section is further configured to change the energy bands so as to increase the width of the energy bands in energy regions having a small change in the value of the raw data, and on the other hand, reduce the width of the energy bands in energy regions having a large change in the value of the raw data.

3. The photon counting type X-ray computed tomography apparatus according to claim 1, wherein
the raw data generating section is further configured to generate raw data of the plurality of energy bands according to an energy threshold value.

4. The photon counting type X-ray computed tomography apparatus according to claim 1, further comprising
a raw data regeneration section configured to receive the transmitted raw data compressed by the information compression and to regenerate raw data of each of the plurality of energy bands on the basis of the received raw data compressed by the information compression.

5. The photon counting type X-ray computed tomography apparatus according to claim 4, further comprising
a memory section configured to store data associated with the received raw data compressed by the information compression.

6. The photon counting type X-ray computed tomography apparatus according to claim 1, wherein on the basis of the generated raw data, the difference calculation processing section is further configured to change the energy bands on the basis of the characteristics represented by the count values.

7. The photon counting type X-ray computed tomography apparatus according to claim 1, wherein on the basis of the generated raw data, the difference calculation processing section is further configured to change the energy bands on the basis of an absorption rate or scattering rate of X-rays.

8. A data transfer method of a photon counting type X-ray computed tomography apparatus including an X-ray tube configured to irradiate an X-ray, and a detector configured to count photons derived from the irradiated X-ray, the data transfer method comprising:
a raw data generation step of collecting results of counting performed by the detector and generating, from the results of counting, raw data for each of a plurality of energy bands;
an information compression step including steps of
selecting for each energy range of energy ranges, one of the plurality of energy bands belonging to the corresponding each energy range as a reference energy band, the energy ranges being divided into the each energy range at an energy where a change amount of count value exceeds a threshold,
setting a raw data of the reference energy band for the each energy range as reference data for the each energy range, and
performing, for the each energy range, information compression of multiple pieces of raw data for energy bands other than the reference energy band by obtaining corresponding multiple pieces of difference data, each piece of difference data being difference between two pieces of raw data of respective two adjacent energy bands belonging to the corresponding each energy range; and
a data transmission step of transmitting the multiple pieces of difference data and the reference data as raw data compressed by the information compression.

\* \* \* \* \*